(12) United States Patent  
Possin et al.

(10) Patent No.: US 7,512,210 B2
(45) Date of Patent: Mar. 31, 2009

(54) HYBRID ENERGY DISCRIMINATING CHARGE INTEGRATING CT DETECTOR

(75) Inventors: George E. Possin, Niskayuna, NY (US); Kent C. Burr, Latham, NY (US); Aaron J. Couture, Schenectady, NY (US); Jonathan D. Short, Saratoga Springs, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 11/692,104

(22) Filed: Mar. 27, 2007

(65) Prior Publication Data

US 2008/0240341 A1 Oct. 2, 2008

(51) Int. Cl.
*G01T 1/24* (2006.01)
(52) U.S. Cl. .................................. 378/19; 250/370.09
(58) Field of Classification Search ............... 378/19, 378/98.8; 250/370.08, 370.09, 370.11
See application file for complete search history.

(56) References Cited

U.S. PATENT DOCUMENTS

2003/0035510 A1* 2/2003 Strommer ................. 378/98.8
2005/0053191 A1* 3/2005 Gohno et al. ................. 378/19
2007/0069142 A1* 3/2007 Moody et al. ........... 250/370.09
2008/0001095 A1* 1/2008 Astley et al. ........... 250/370.09

OTHER PUBLICATIONS

SensL Sensors for Nuclear Medicine.
ROF PET CEO Project Topic: alternative photosensors, Solid-State Photo-Multipliers, Jul. 12, 2005.
Z. Sadygov, "Three advanced designs of avalanche micro-pixel photodiodes . . . " Beaune 2005.
J.C. Jackson et al., "Toward Integrated Single-Photon-Counting Microarrays," Opt. Eng. 42(1) 112-118 (Jan. 2003).

* cited by examiner

*Primary Examiner*—Hoon Song
(74) *Attorney, Agent, or Firm*—Jason K. Klindtworth

(57) ABSTRACT

An imaging system includes a gantry having a bore therethrough designed to receive a patient being translated through the bore an x-ray source disposed in the gantry and configured to emit x-rays toward the patient, and a detector module disposed in the gantry to receive x-rays attenuated by the patient. The detector module includes a scintillator configured to absorb the x-rays and to convert the x-rays into optical photons, a device configured to receive the optical photons and to convert the optical photons to electrical signals, and an adaptive data acquisition system (DAS) configured to switch an operating mode of the device from a charge integrating mode to a photon counting mode, and vice versa.

31 Claims, 7 Drawing Sheets

HYBRID ENERGY DISCRIMINATING CHARGE INTEGRATING CT DETECTOR

BACKGROUND OF THE INVENTION

The present invention relates generally to radiographic detectors for diagnostic imaging and, more particularly, to a CT detector capable of providing photon count and energy data with improved saturation characteristics having an adaptive data acquisition circuit (DAS) circuit to rapidly switch between charge integrating and photon counting modes.

Typically, in radiographic imaging systems, such as x-ray and computed tomography (CT), an x-ray source emits x-rays toward a subject or object, such as a patient or a piece of luggage. Hereinafter, the terms "subject" and "object" may be interchangeably used to describe anything capable of being imaged. The beam, after being attenuated by the subject, impinges upon an array of radiation detectors. The intensity of the attenuated beam radiation received at the detector array is typically dependent upon the attenuation of the x-rays. Each detector element of the detector array produces a separate electrical signal indicative of the attenuated beam received by each detector element. The electrical signals are transmitted to a data processing system for analysis which ultimately produces an image.

Conventional CT imaging systems utilize detectors that convert radiographic energy into current signals that are integrated over a time period, then measured and ultimately digitized. A drawback of such detectors however is their inability to provide data or feedback as to the number and/or energy of photons detected. During image reconstruction, data as to the number and/or energy of photons detected can be used to distinguish materials which appear identical in images reconstructed from conventional systems that do not provide this additional information. That is, conventional CT detectors have a scintillator component and photodiode component wherein the scintillator component illuminates upon reception of radiographic energy and the photodiode detects illumination of the scintillator component and provides an electrical signal as a function of the intensity of illumination. A drawback of these detectors is their inability to provide energy discriminatory data or otherwise count the number and/or measure the energy of photons actually received by a given detector element or pixel. That is, the light emitted by the scintillator is a function of the number of x-rays impinged as well as the energy level of the x-rays. Under the charge integration operation mode, the photodiode is not capable of discriminating between the energy level or the photon count from the scintillation. For example, two scintillators may illuminate with equivalent intensity and, as such, provide equivalent output to their respective photodiodes. Yet, the number of x-rays received by each scintillator may be different as well as the x-rays' energy, but yield an equivalent light output.

In attempts to design scintillator based detectors capable of photon counting and energy discrimination, detectors constructed from scintillators coupled to either avalanche photodiodes (APDs) or photomultipliers have also been employed. However, there are varying problems that limit the use of these detectors. In the case of APDs, there is additional gain need to enable photon counting, but with associated gain-instability noise, temperature sensitivity, and other reliability issues. In the case of photomultiplier tubes, these devices are too large, mechanically fragile, and costly for high resolution detectors covering large areas as used in CT. As such, these photomultiplier tubes have been limited to use in PET or SPECT systems.

To overcome these shortcomings, energy discriminating, direct conversion detectors capable of not only x-ray counting, but of also providing a measurement of the energy level of each x-ray detected have been employed in CT systems. A drawback of direct conversion semiconductor detectors, however, is that these types of detectors cannot count at the x-ray photon flux rates typically encountered with conventional CT systems. That is, the CT system requirements of high signal-to-noise ratio, high spatial resolution, and fast scan time dictate that x-ray photon flux rates in a CT system be very high, e.g. at or greatly exceeding 1 million x-rays per sec per millimeter squared. Also, the count rate in a single detector pixel, measured in counts per second (cps) and determined by the flux rate, the pixel area, and the detection efficiency, is very high. The very high x-ray photon flux rate causes pile-up and polarization. "Pile-up" is a phenomenon that occurs when a source flux at the detector is so high that there is a non-negligible possibility that two or more x-ray photons deposit charge packets in a single pixel close enough in time so that their signals interfere with each other. Pile-up phenomenon are of two general types, which result in somewhat different effects. In the first type, the two or more events are separated by sufficient time so that they are recognized as distinct events, but the signals overlap so that the precision of the measurement of the energy of the later arriving x-ray or x-rays is degraded. This type of pile-up results in a degradation of the energy resolution of the system. In the second type of pile-up, the two or more events arrive close enough in time so that the system is not able to resolve them as distinct events. In such a case, these events are recognized as one single event having the sum of their energies and the events are shifted in the spectrum to higher energies. In addition, pile-up leads to a more or less pronounced depression of counts in high x-ray flux, resulting in detector quantum efficiency (DQE) loss.

Direct conversion detectors are also susceptible to a phenomenon called "polarization" where charge trapping inside the material changes the internal electric field, alters the detector count and energy response in an unpredictable way, and results in hysteresis where response is altered by previous exposure history. This pile-up and polarization ultimately leads to detector saturation, which as stated above, occurs at relatively low x-ray flux level thresholds in direct conversion sensors. Above these thresholds, the detector response is not predictable and has degraded dose utilization that leads to loss of imaging information and results in noise and artifacts in x-ray projection and CT images. In particular, photon counting, direct conversion detectors saturate due to the intrinsic charge collection time (i.e. dead time) associated with each x-ray photon event. Saturation will occur due to pulse pile-up when x-ray photon absorption rate for each pixel is on the order of the inverse of this charge collection time.

In attempts to design scintillator-based detectors capable of photon counting and energy discrimination, detectors constructed from scintillators coupled to solid state photomultiplier (SSPMs) configured to operate in Geiger-mode have been proposed. At count rates up to, for instance, $1 \times 10^7$ cps, a scintillator/SSPM combination can adequately count x-rays in photon count mode, thereby providing energy discriminating information. For count rates above, for instance, $1 \times 10^7$ cps, counts may be lost if the scintillator/SSPM is operating in a photon count mode, and the scintillator/SSPM may be operated in charge integrating, or energy integrating, mode to collect non-spectral charge integrating data. However, data can be lost if the switching between modes is too long, too frequent, or it not timed to occur properly during the data acquisition sequence.

It would therefore be desirable to design an adaptive DAS to rapidly switch control of the scintillator/SSPM between photon counting and charge integrating modes. It would be further desirable to design the DAS such that switching between photon counting modes and charge integrating modes occurs between views to minimize lost data. It would also be desirable to design the DAS such that cycling is minimized between modes while keeping as many detectors as possible in photon counting mode. It would further be desirable to minimize the number of electrical components in the adaptive DAS.

BRIEF DESCRIPTION OF THE INVENTION

The present invention overcomes the aforementioned drawbacks by providing an adaptive DAS that can rapidly switch operation of a SSPM/scintillator between photon counting and charge integrating modes.

According to one aspect of the present invention, an imaging system includes a gantry having a bore therethrough designed to receive a patient being translated through the bore an x-ray source disposed in the gantry and configured to emit x-rays toward the patient, and a detector module disposed in the gantry to receive x-rays attenuated by the patient. The detector module includes a scintillator configured to absorb the x-rays and to convert the x-rays into optical photons, a device configured to receive the optical photons and to convert the optical photons to electrical signals, and an adaptive data acquisition system (DAS) configured to switch an operating mode of the device from a charge integrating mode to a photon counting mode, and vice versa.

In accordance with another aspect of the present invention, a detector module includes a data acquisition system (DAS) configured to automatically switch operation of a solid-state photomultiplier (SSPM) between an energy integrating mode and a photon counting mode and automatically switch operation of the SSPM between the photon counting mode and the energy integrating mode.

In accordance with yet another aspect of the present invention, a method for constructing a detector includes the steps of forming a scintillator to receive x-rays and convert the x-rays into optical photons, optically coupling a solid-state photomultiplier (SSPM) to the scintillator, the SSPM configured to receive and convert the optical photons into a corresponding electrical signal output, electrically connecting a data acquisition system (DAS) to the SSPM to receive the electrical signal output therefrom, and configuring the DAS to automatically switch operation of the SSPM between a charge integrating mode and a photon counting mode, and vice versa.

Various other features and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION OF THE INVENTION

In accordance with one aspect of the present invention, a CT imaging system is provided. The CT imaging system includes a detector constructed to perform photon counting and energy discrimination of x-rays at the high flux rates generally associated with CT imaging, and includes an adaptive DAS to rapidly switch between charge integrating and photon counting modes with appropriate timing during data acquisition.

The operating environment of the present invention is described with respect to a sixty-four-slice computed tomography (CT) system. However, it will be appreciated by those skilled in the art that the present invention is equally applicable for use with other multi-slice configurations. Moreover, the present invention will be described with respect to the detection and conversion of x-rays. However, one skilled in the art will further appreciate that the present invention is equally applicable for the detection and conversion of other high frequency electromagnetic energy. The present invention will be described with respect to a "third generation" CT scanner, but is equally applicable with other CT systems.

Figure 1:
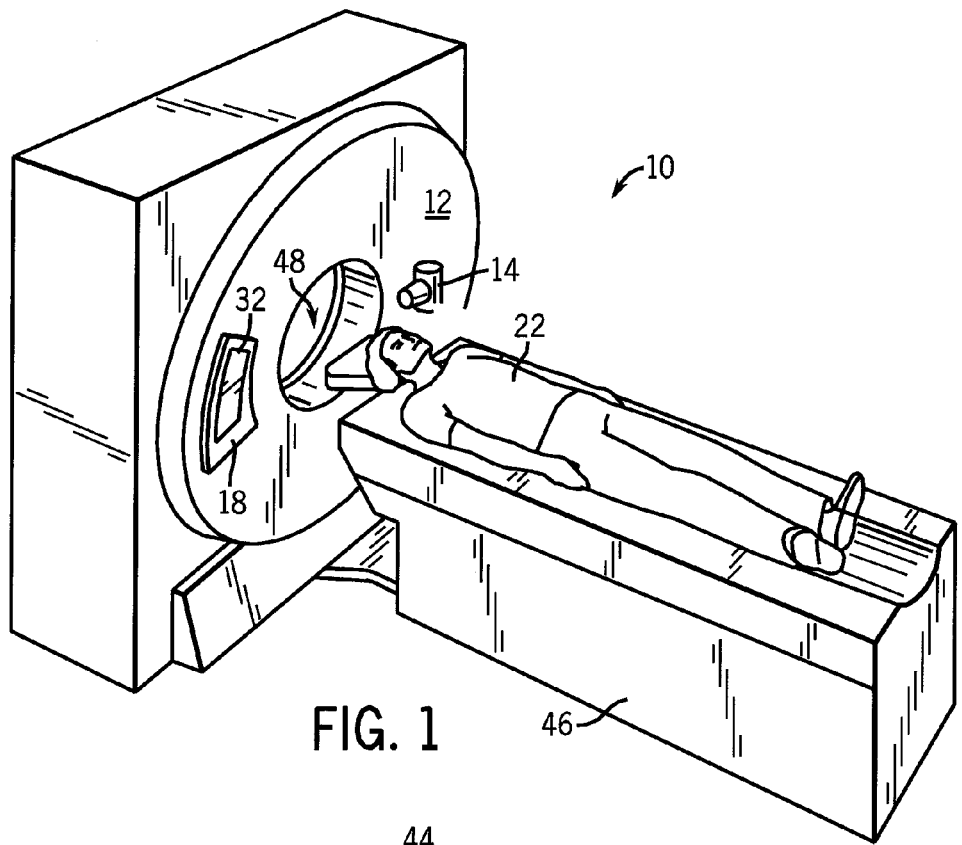
FIG. 1 is a pictorial view of a CT imaging system of the current invention.
Figure 2:
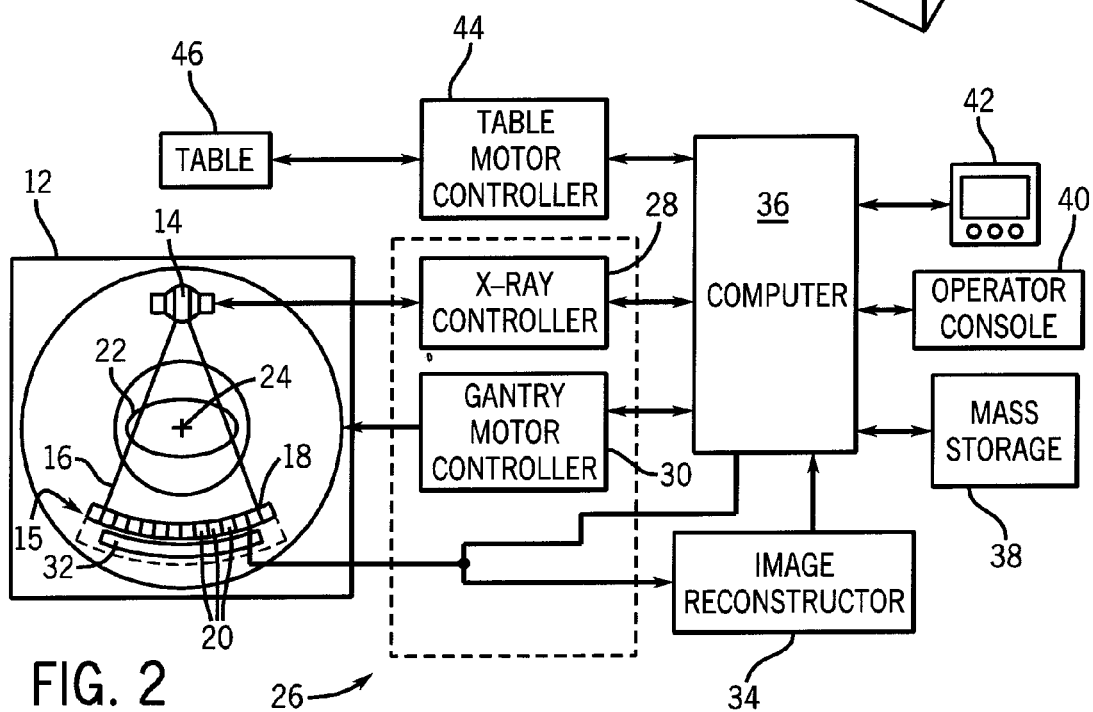
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector assembly 15 on the opposite side of the gantry 12. The detector assembly 15 includes therein a collimator assembly 18, a plurality of detector modules 20, and data acquisition systems (DAS) 32. In one embodiment, detector assembly 15 includes fifty-seven detector modules 20, with each detector module 20 having an array size of 64×16 of pixel elements. As a result, detector assembly 15 has 64 rows and 912 columns (16×57 detectors) which allows 64 simultaneous slices of data to be collected with each rotation of gantry 12. The plurality of detector modules 20 sense the projected x-rays that pass through a medical patient 22, and DAS 32 converts the data to digital signals for subsequent processing. Each detector module 20 in a conventional system produces an analog electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves portions of patient 22 through a gantry opening 48.

Figure 3:
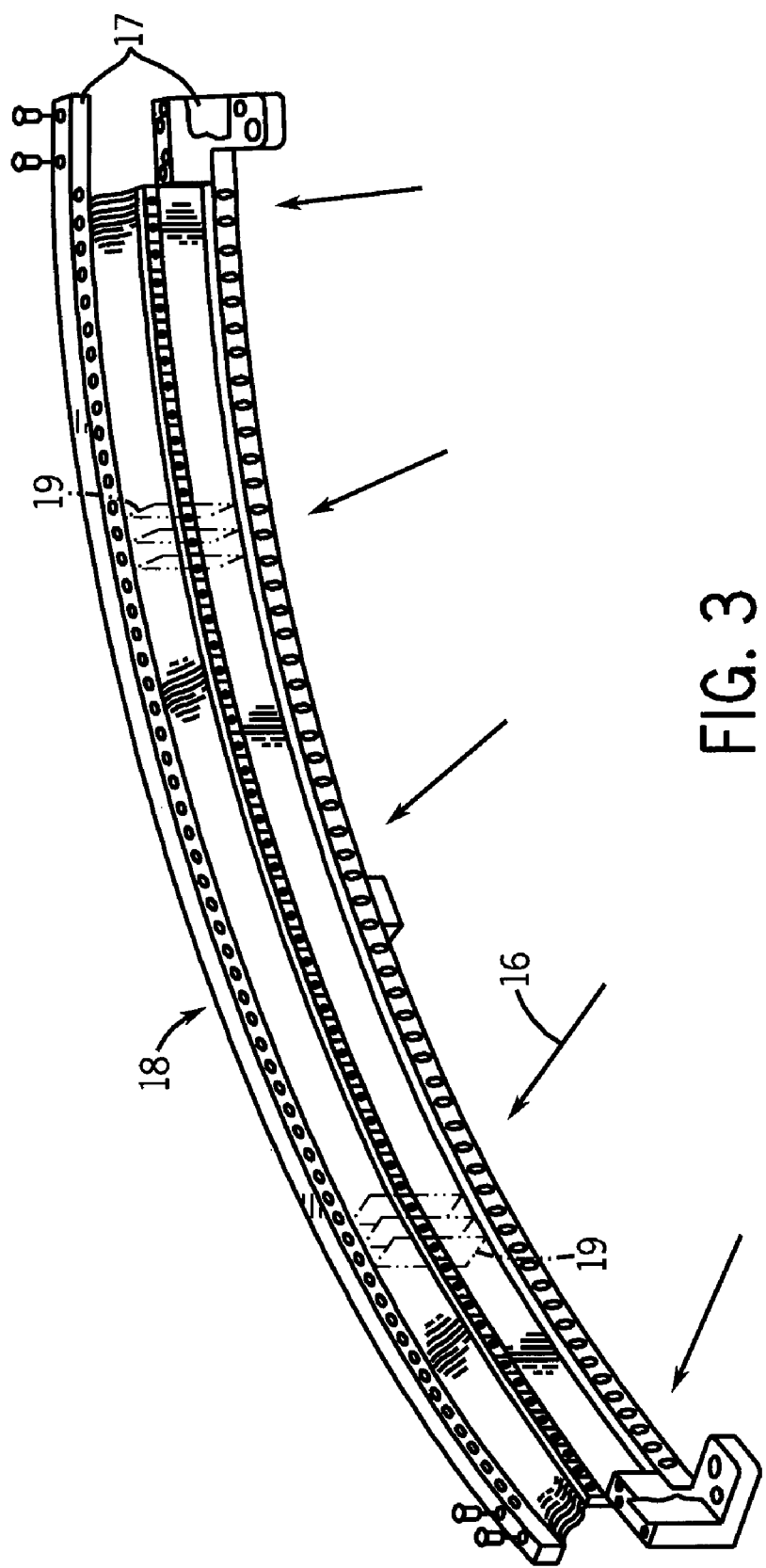
FIG. 3 is a perspective view of one embodiment of a CT system collimator assembly.

As shown in FIG. 3, collimator assembly 18 includes rails 17 having collimating blades or plates 19 placed therebetween. Collimator assembly 18 is positioned in such a way so that x-rays 16 are collimated by the collimating blades 19 before such beams impinge upon the detector module 20 (shown in FIG. 2).

Figure 4:
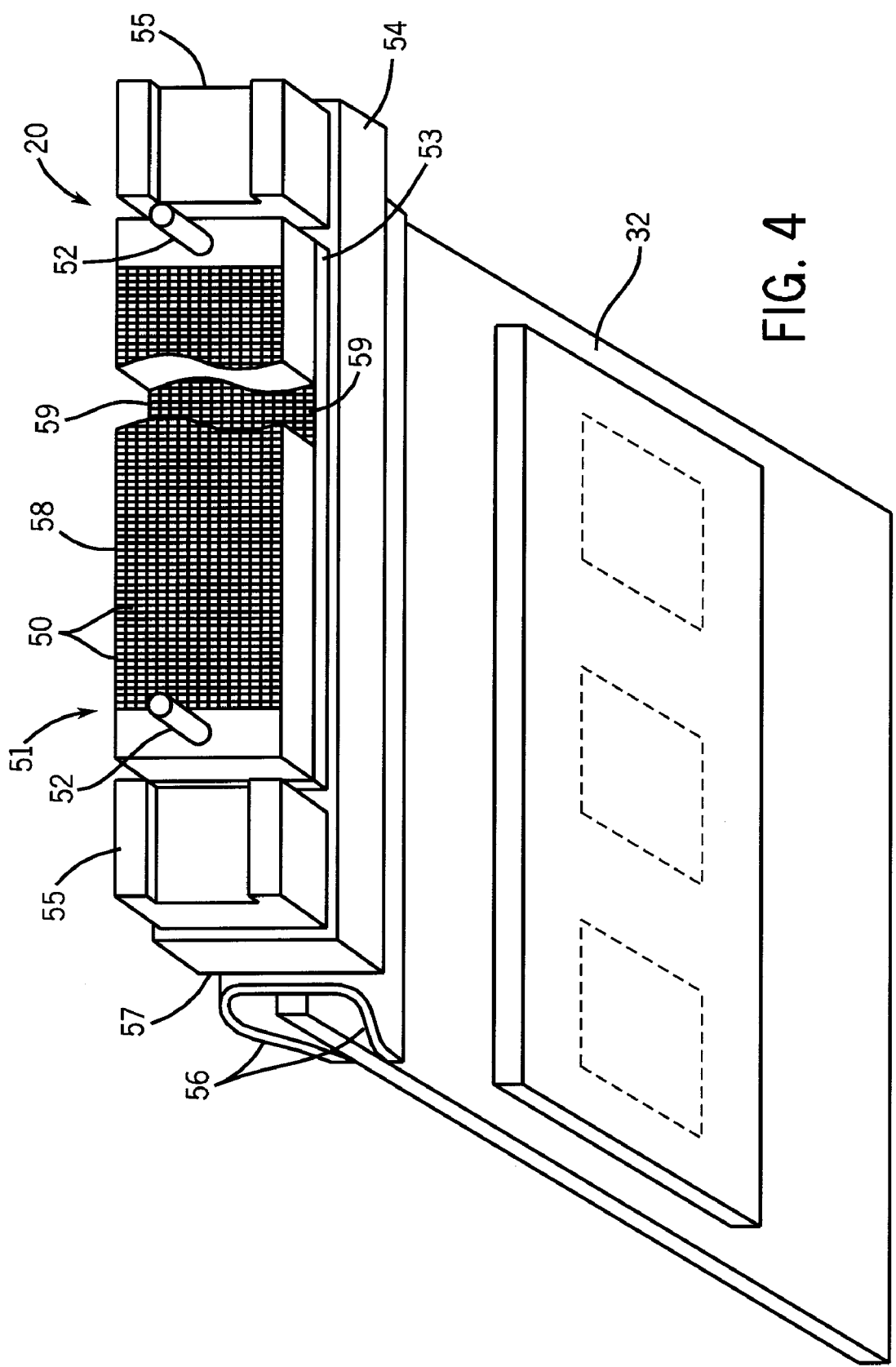
FIG. 4 is a perspective view of one embodiment of a detector module.

Referring now to FIG. 4, detector module 20 includes DAS 32 and is further comprised of a number of scintillator elements 50 arranged in pack 51. Detector module 20 includes pins 52 positioned within pack 51 relative to scintillator elements 50. Pack 51 is positioned on photosensor 53, which is in turn positioned on multi-layer substrate 54. Spacers 55 are positioned on multi-layer substrate 54. Scintillator elements 50 are optically coupled to photosensor 53, and photosensor 53 is in turn electrically coupled to multi-layer substrate 54. Flex circuits 56 are attached to face 57 of multi-layer substrate 54 and to DAS 32. Detector module 20 is positioned within collimator assembly 18 by use of pins 52.

In the embodiment of detector module 20 shown in FIG. 4, pack 51 includes pins 52, a scintillator 58, and a reflective material (not shown) positioned between individual scintillator elements 50, (i.e., pixel elements) that form scintillator 58. Scintillator 58 is positioned to receive impinging x-rays 16 and generate light photons responsive thereto. The light photons traverse scintillator 58 and are received by a solid-state photosensor 53 (i.e., a solid-state photomultiplier (SSPM)), which converts the light photons into analog electrical signals. The analog signal generated is carried through a multi-layer substrate 54 to DAS 32, wherein the analog signal is converted to a digital signal.

To improve the photon counting capabilities of detector module 20 over that of existing direct conversion semiconductor detectors, scintillator 58 is designed to have a rapid decay time for the photons generated therein that is faster than charge can typically be collected in direct conversion semiconductors. To optimize performance of the scintillator 58 and achieve this rapid decay time, scintillator is composed of a "fast" scintillator material. In one embodiment, scintillator 58 is composed of a ceramic scintillation material. This material can take the form of, for example, $(Lu_xTb_{1-x-y}Ce_y)_3Al_5O_{12}$ (i.e., LuTAG), where "x" ranges from 0.5 to 1.5 and "y" ranges from 0.01 to 0.15. For instance, the proper ratio may be defined by the following stoichiometrical equation, $Lu_{0.8}Tb_{2.17}Ce_{0.03}Al_5O_{12}$, although one skilled in the art would readily recognize that other composition ratios may be possible as well. Other scintillation materials may also be used, such as LYSO, $LaBr_3$ (lanthanum bromide), or some other suitable material.

The fast scintillator material has a primary fluorescence decay time of less than 50 nanoseconds. The value of the decay time is indicative of the afterglow of light for a scintillator material subsequent to the ceasing of the high frequency electromagnetic energy projection toward the scintillator 58. This fast decay speed lessens the so-called "dead time" the detector module 20 will have and increases the number of ionizing events per unit of time each of the scintillator elements 50 are able to detect. Lessening of the dead time allows the scintillator elements 50 to handle higher count rates without suffering long-term instabilities, which aids in the prevention of saturation and, in the event of saturation, allows for faster recovery of within 1-2 view periods.

Scintillator 58 is also preferably constructed as a pixelated scintillator 58 formed of a single crystal block. The scintillator block is pixelated using a method well known in the art that is able to produce a high resolution scintillator 58 having small pixel size and narrow inter-pixel gaps. As will be discussed in greater detail below, the pixelated scintillator 58 design provides for high quality optical coupling between the scintillator 58 and the SSPM 53 by matching up scintillator pixels 50 with pixels 59 on the SSPM. The combination of the fast scintillator material and the pixelated design described above allows for enhanced sensitivity and light collection that allows the detector module 20 to achieve photon counting and energy discrimination at high flux rates.

As stated above, fast scintillator 58 provides for improved photon counting of x-rays by accommodating high flux rates. However, the number of optical photons generated by the scintillator 58 is relatively low. To overcome the low number of optical photons generated by x-ray absorption in scintillator 58 (i.e., the low signal level), solid-state photomultipler (SSPM) 53 is combined with scintillator 58 to provide fast, proportional amplification of the signals. SSPM 53 is comprised of a solid semiconductor material and, in one embodiment, is formed as a silicon photomultiplier (SiPM), although it is envisioned that other suitable materials could also be used.

Figure 5:
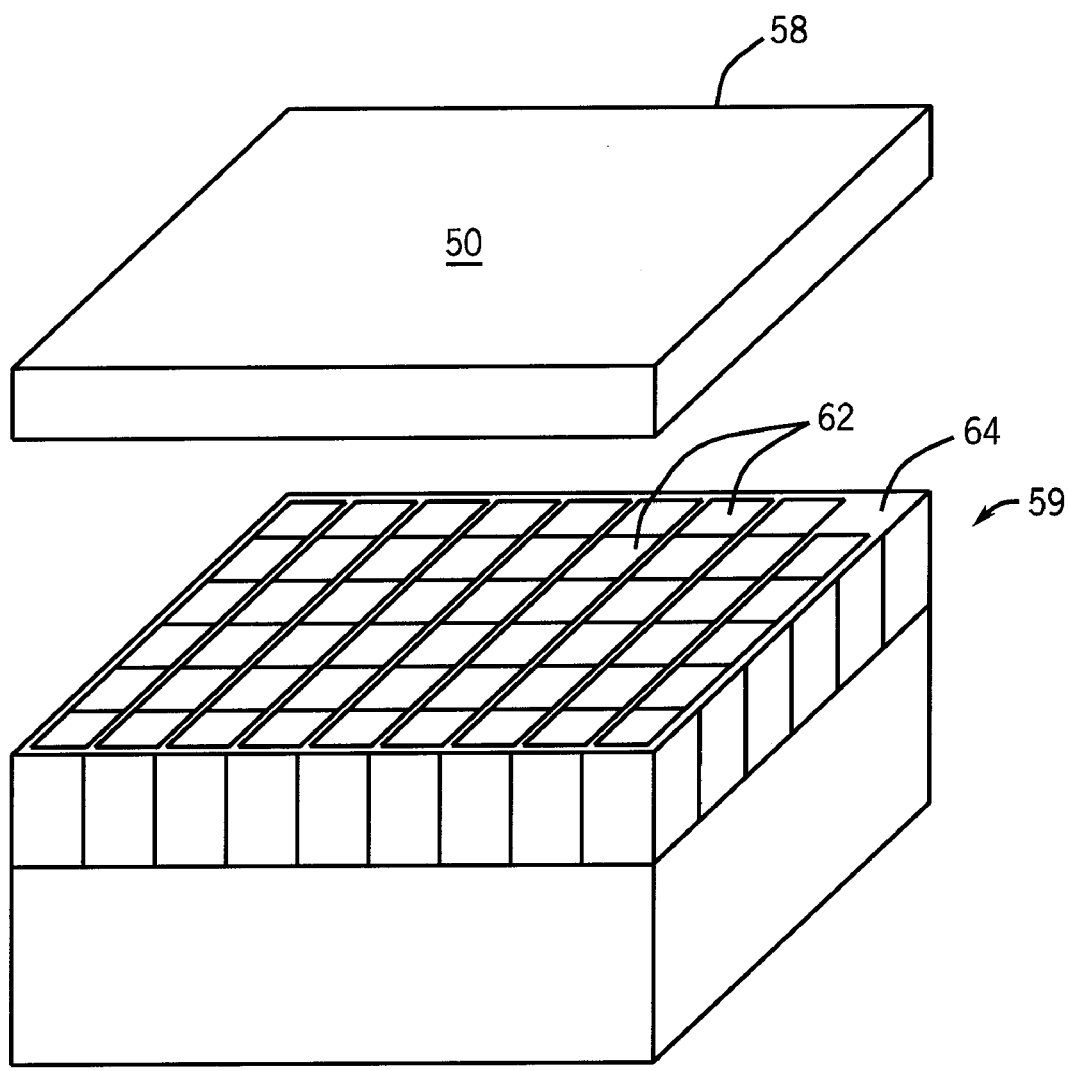
FIG. 5 is a perspective view of a detector pixel according to the current invention.

SSPM 53 is comprised of a plurality of macroscopic units referred to as pixels 59. The number of pixels 59 on the SSPM 53 should be sufficient to cover an area of the detector module 20 and correspond to the pixelated scintillator 58 and the pixel elements 50 thereon, although the exact number and density of the pixels 59 will be determined by image resolution desired by an operator and other known factors. A portion of a pixel 59 is shown in FIG. 5 as being comprised of a plurality of avalanche photodiodes (APDs) or "microcells" 62 that amplify single optical photon arrivals from the scintillator 58 into a large signal. Typically, each pixel 59 will contain between 100 to 2500 APDs per $mm^2$, with each of the microcells 62 having a length of 20-100 microns. Each of the microcells 62 operates as an individual Geiger-mode APD a few volts above a breakdown voltage, with each microcell 62 being virtually identical to all the other microcells. In this mode of operation, an electron generated by the absorption of an optical photon initiates an avalanche breakdown that is confined to an individual microcell 62 when the one or more photons is absorbed by that microcell. A single discrete unit of electrical charge is emitted from the microcell 62 independent of the number of photons absorbed therein. That is, for each Geiger breakdown, the output signal of the microcell 62 will have the same shape and charge, except for small variations due to differences from cell to cell introduced in the production process.

Figure 6:
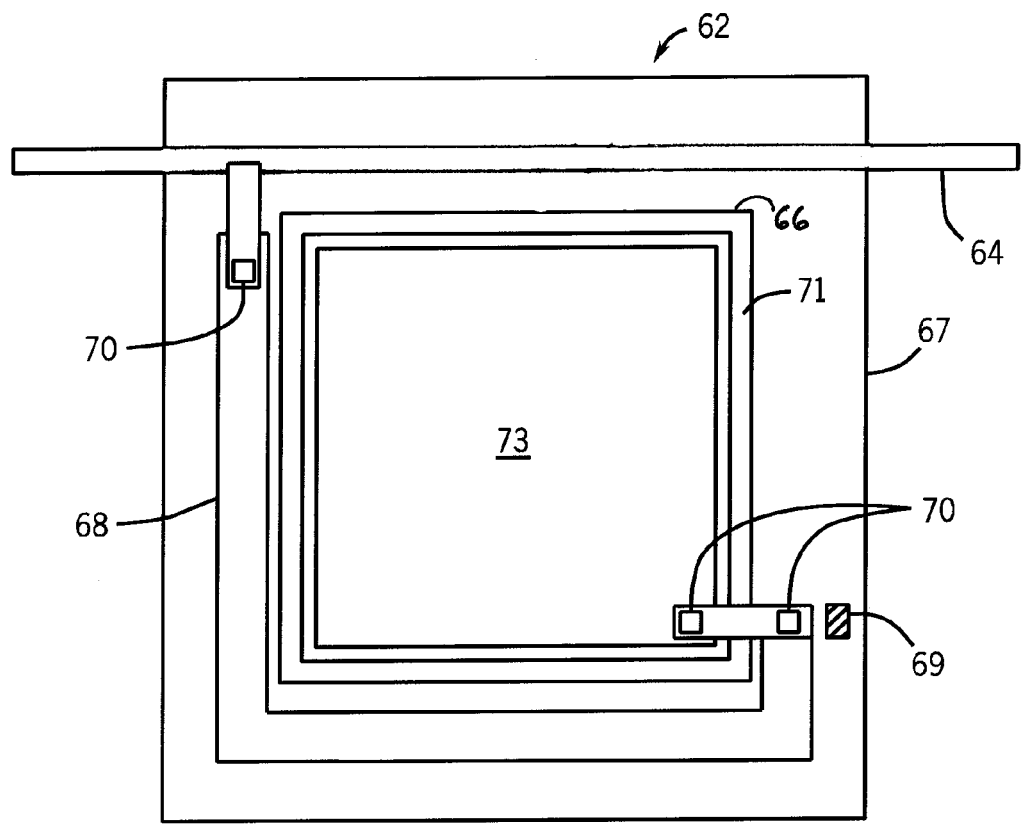
FIG. 6 is a top plan view of a microcell according to the current invention.
Figure 7:
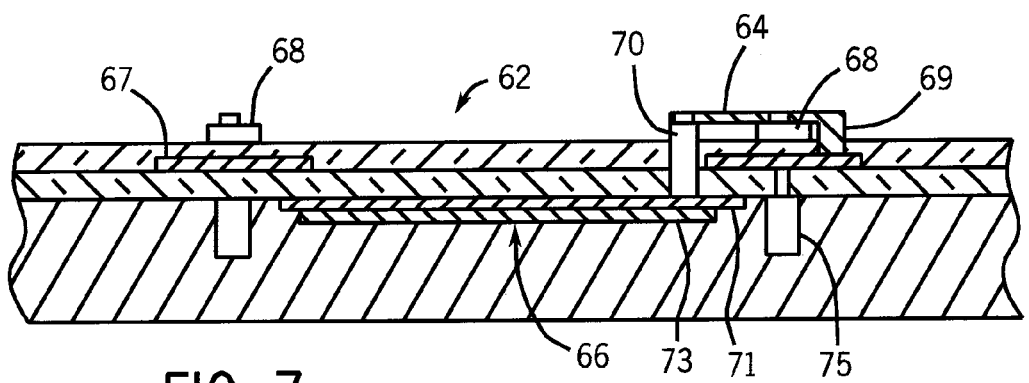
FIG. 7 is a side elevational view of the microcell of FIG. 6.

Each microcell 62 is connected to a conductive grid 64 on the front side of the pixel 59. In one embodiment, the conductive grid 64 is composed of aluminum, although other similar materials are also envisioned that are conductive and also, preferably, non-magnetic. As shown in FIGS. 6 and 7, each microcell 62 includes an active area 66 surrounded by a metal light shield/cathode 67 that includes a cathode contact 69 thereon. While front side contacts are shown in FIGS. 6 and 7, the cathode contact could be made on the back side of the wafer or thru-vias could be used for both anode and cathode contacts to provide back side connections. The active area 66 is comprised of a P+ anode 71 and an N implant 73 to convert optical photons into a corresponding electrical signal. The active area 66 is, in part, separated from the remainder of microcell 62 by an N+ guard.

Connection between active area 66 of each microcell 62 and the conductive grid 64 is formed by way of a resistor 68, composed of polysilicon in one embodiment. The resistor 68 is connected to the active area 66 of microcell 62 by way of vias 70 and functions to limit the current transferred from the microcell 62 to the conductive grid 64. The resistor 68 also serves to quench the avalanche in the microcell 62 once the cell capacity discharges. By way of resistors 68 and conductive grid 64, the independently operating APD cells 62 are electrically connected and the individual outputs of all the microcells 62 are summed to form a common readout signal. The common readout signal that is output from the pixel 59 is thus the superposition of the standardized signals of all fired microcells 62. That is, the output of each pixel 59 of FIG. 5 is determined by the sum of the discrete electrical charge units from the microcells 62 that fire. As such, the output of the pixel 59 of FIG. 5 is dependent on the number of microcells 62 that absorb a photon rather than the number of photons absorbed by each microcell 62. The resulting output from each pixel 59 is in the form of an analog pulse with a charge that is proportional to the number of absorbed photons.

As described above, the array of microcells 62 in each pixel 59 amplify single optical photon arrivals into a large signal by way of the individual APD elements 62 operating in Geiger-mode. The structure of the pixel 59 provides nearly noiseless, high gain amplification in the range of $10^5$-$10^6$, such that even a single optical photon can be easily detected and resolved, thus eliminating the need for additional preamplifiers. This gain can be achieved at a relatively low bias or supply voltage range of about 30-70 V.

Referring back to FIG. 4, connected to SSPM 53 is a data acquisition system (DAS) 32, i.e., readout electronics, that receive electrical signals from the SSPM 53 and performs further processing thereon. Because the combination of the scintillator 58 and SSPM 53 allows for electrical signal collection faster than the charge collection time of direct conversion sensors (i.e., CZT/CdTe detectors), which are limited by the mobility of charge carriers in those materials, the DAS 32 is able to operate at high count rates that are desired in CT imaging and that were not otherwise available with previous designs. The improved electrical signal collection, along with the low noise environment of the SSPM 53, allows for the DAS 32 to perform photon counting at a high count rate typically greater than $1 \times 10^7$ cps. Operation at these count rates minimizes the occurrence or probability of problems related to detector saturation by providing the capability to handle high flux rates without suffering long-term instabilities. By careful design of the number of microcells 62 within each pixel 59 of the SSPM 53 and by controlling the light output of the scintillator 58, it is also possible to allow for count rates in the DAS 32 greater than the primary decay speed of a single excitation in the scintillator 58.

In addition to photon counting, the electrical signals output by the SSPM 53 also allow the DAS 32 to perform an energy discrimination analysis in regards to the emitted x-rays 16. That is, using the intensity of the signal arriving from the SSPM 53, the DAS 32 is able to characterize the energy of the original x-rays 16 and separate them into two or more energy bins. At a minimum, the original x-rays 16 could be characterized as either high or low energy and thus separate the x-rays into high and low energy bins. This energy discrimination function is important in the lower flux levels of an image where x-ray and electronic noise are most important, this level typically being up to $1 \times 10^7$ x-rays per sec per millimeter squared.

While the detector 20 described above is configured to perform photon counting and energy discrimination of the x-rays 16 received by the detector, it is also envisioned that the detector 20 can operate in a charge integration mode. In this charge integration mode, detector 20 converts x-ray energy into current signals that are integrated over a time period, then measured and ultimately digitized by the DAS 32. Operating in charge integration mode allows detector 20 to accommodate even higher flux rates than when in energy discrimination mode, these flux rates being in the range exceeding approximately $1 \times 10^9$ x-rays per sec per millimeter squared. Furthermore, while the electrical circuit described herein is described relative to a CT imaging system, one skilled in the art will recognize that the technique described herein may be used in other light sensing and imaging systems. In particular, it may be used in a light-sensing application other than a device that uses a scintillator for detecting ionizing radiation.

Figure 8:
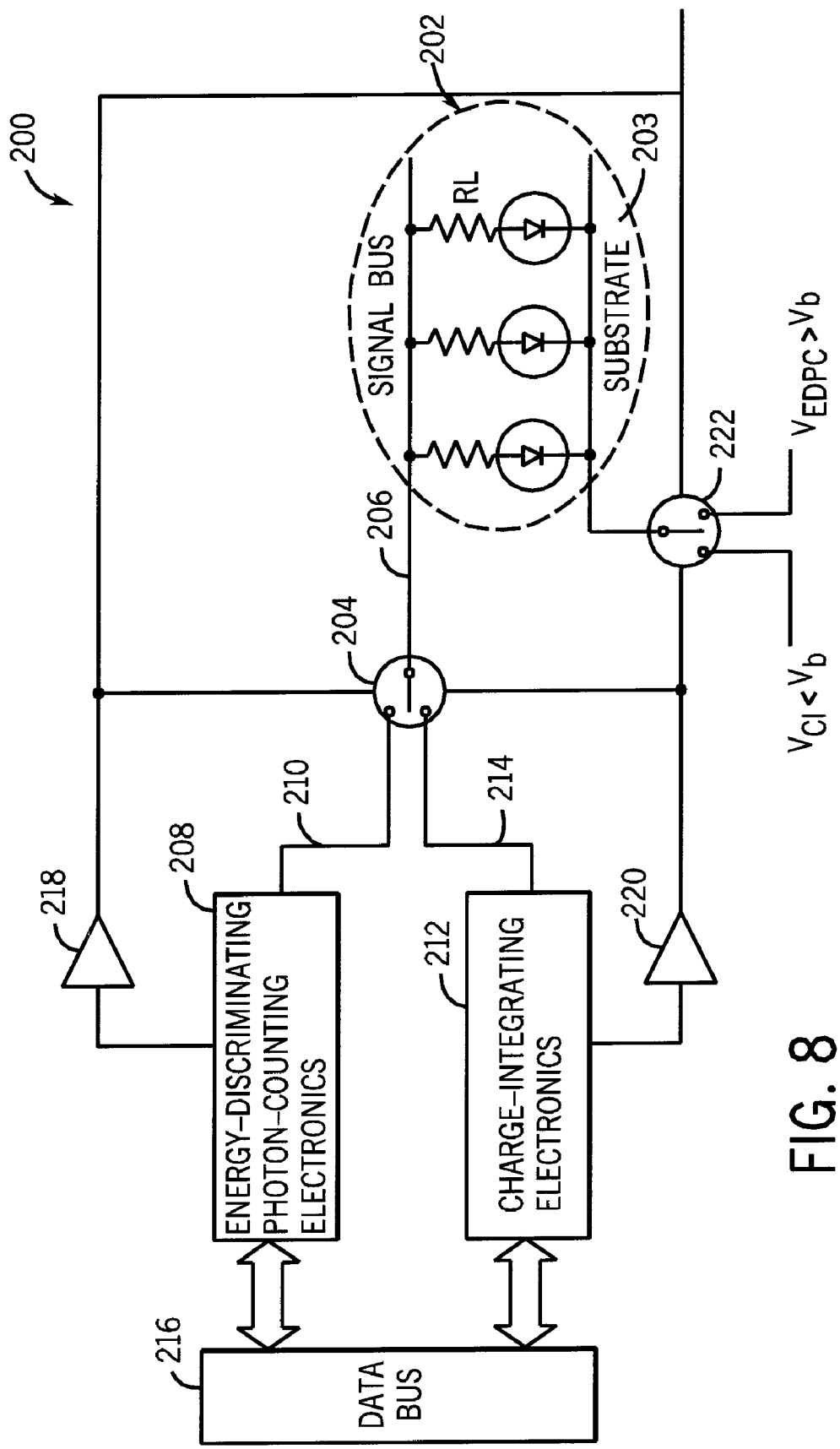
FIG. 8 is an adaptive DAS circuit according to an embodiment of the current invention.

FIG. 8 shows a DAS schematic block diagram of a circuit 200 configured to switch operation of detector 20 between the photon counting mode and the charge integrating mode according to an embodiment of the present convention. An APD (SSPM) 202 configured to operate in Geiger-mode is schematically shown having a substrate 203. A switch 204 receives analog signals from APD 202 along connection 206 and directs the analog signals to either a system of Energy-Discriminating Photon-Counting electronics (hereinafter "PC electronics") 208 along connection 210 or to a system of Charge-Integrating electronics (hereinafter "CI electronics") 212 along connection 214. PC electronics 208 and CI electronics 212 may be implemented in a number of ways that are well understood by one skilled in the art. PC electronics 208 and CI electronics 212 each include an analog-to-digital converter (not shown) that convert received analog signals into digital signals. Digital signals generated from both sets of electronics 208, 212 are directed to a data bus 216 that transfers the digital signals to an image reconstructor such as the image reconstructor 32 shown in FIG. 2.

A logic switch 218 is connected between the PC electronics 208 and switch 204. Logic switch 218 receives an input from the PC electronics 208 if a maximum count rate exceeds a threshold, $C_{max}$, as determined by the PC electronics 208. $C_{max}$ is a threshold representing a maximum count rate that defines the point where the DAS circuit 200 causes switch 204 to switch operation of the APD 202 and the electronics from a photon counting mode to a charge integrating mode. $C_{max}$ is chosen such that an appropriate balance is struck between loss of DQE while minimizing excessive cycling between modes, and while keeping the detectors in photon counting mode as much as possible. At count rates below, for instance $1 \times 10^7$ cps, the scintillator/SSPM combination can adequately count x-rays in photon counting mode, thereby providing energy discriminating information. However, for count rates above $1 \times 10^7$ cps, counts may be lost and there is a degradation of DQE. Accordingly, $C_{max}$ may be set to, for instance, $2 \times 10^7$ cps, in order to accept some loss of DQE while minimizing the amount of transitions between modes. Upon receipt of the input from the PC electronics 208, logic switch 218 causes switch 204 to transfer analog signals from APD 202 to CI electronics 212 along connection 214.

In addition to being connected between the PC electronics 208, logic switch 218 is also connected between the PC electronics 208 and a switch 222 that determines a bias voltage of substrate 203. APD (SSPM) 202 has breakdown voltage $V_b$ associated therewith, and switch 222 determines a bias voltage that is directed to substrate 203. When circuit 200 operates in energy integrating mode, then a preferred bias voltage, $V_{CI}$, applied to substrate 203 is below $V_b$, typically close to 0V. When circuit 200 operates in photon counting mode, then a preferred bias voltage, $V_{EDPC}$, applied to substrate 203 is above $V_b$. Accordingly, upon receipt of the input from the PC electronics 208, logic switch 218 causes switch 222 to switch the bias voltage applied to substrate 203 to an energy integrating bias voltage, e.g., from $V_{EDPC}$ to $V_{CI}$.

Still referring to FIG. 8, a logic switch 220 is connected between the CI electronics 212 and switch 204. Logic switch 220 receives an input from the CI electronics 212 if a minimum detector charge falls below a threshold, $Q_{min}$, as determined by the CI electronics 208. $Q_{min}$ is a minimum detector charge selected that defines the point where the DAS circuit switches from energy integrating mode to photon counting mode. $Q_{min}$, as well, is chosen to minimize excessive switching between modes. $Q_{min}$ may be calculated in the following fashion:

$$Qmin=H*Cmax*Q0*V;$$

where H is an adjustable parameter based on data and is chosen to minimize excessive switching between modes while keeping as many detectors as possible in photon counting mode. Cmax is the value determined as described above and is the set point where switching occurs between photon counting and energy integrating modes. Q0 is the average charge signal per x-ray. V is the time per view, which is dependent on at least detector geometry and the gantry rotation speed.

In addition to being connected between the CI electronics 212, logic switch 220 is also connected between the CI electronics 212 and switch 222. Upon receipt of the input from the CI electronics 212, logic switch 220 causes switch 204 to transfer analog signals from APD 202 to PC electronics 208 along connection 210. Furthermore, logic switch 220 causes switch 222 to switch the bias voltage applied to substrate 203 to a photon counting bias voltage, e.g., $V_{CI}$ from to $V_{EDPC}$.

Accordingly, logic switches 218, 220, connected to switch 204 as described above, are likewise connected to switch 222 and send a logic signal thereto. Accordingly, when circuit 200 is operating in energy discriminating/photon counting mode, and when the count rate from PC electronics 208 exceeds $C_{max}$, then logic signal 218 will direct switch 222 to pass the preferred bias voltage for charge integrating operation to substrate 203 and the output 206 of the APD (SSPM) 202 will be connected to the input 214 of the charge integrating electronics 212. Likewise, when circuit 200 is operating in charge integrating mode, and when the charge from CI electronics 212 drops below $Q_{min}$, then logic signal 220 will direct switch 222 to pass the preferred bias voltage for photon counting to substrate 203 and the output 206 of the APD (SSPM) will be connected to the input 210 of the photon counting electronics.

In operation, circuit 200 optimally switches operation of the APD 202 and the analog-to-digital converters of PC electronics 208 and CI electronics 212 between energy integrating and photon counting modes in as little as 10 nsecs. $Q_{min}$ and $C_{max}$ are appropriately determined by striking a balance between maximizing DQE for detectors operating in photon counting mode, yet keeping the transition points separated enough so that circuit 200 does not thrash, or change modes too frequently. Circuit 200 may be designed to further limit the number of transitions by switching between modes only when $C_{max}$ is exceeded, or $Q_{min}$ is not exceeded, for more than, for instance, two views within a scan. Circuit 200 may be further designed to switch between modes, once the determination has been made to do so, only between views, in order to further minimize lost data. Furthermore, circuit 200 may be locked in one mode of operation or another, by setting switches 204 and 222 for the duration of a scan. Accordingly, the operating mode of circuit 200 may be switched between scans. Additionally, since switching between charge integrating and photon counting modes may occur in as little as 10 nsecs, data loss due to such switching may be minimized.

Figure 9:
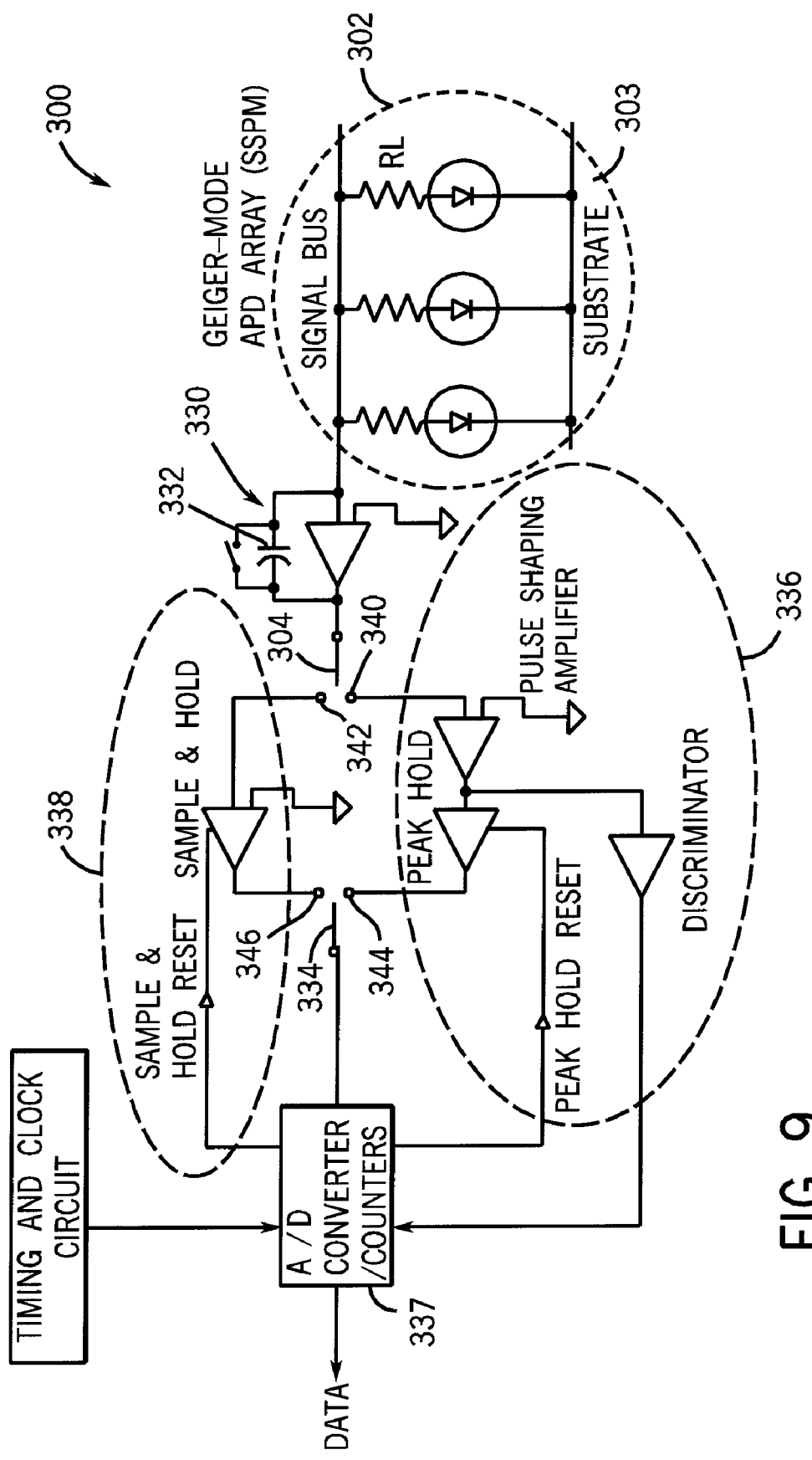
FIG. 9 is a portion of an adaptive DAS circuit illustrating shared components according to an embodiment of the current invention.

Referring to FIG. 9, a portion of a circuit 300 is shown having shared components between the PC electronics 336 and the CI electronics 338 that could be used in the circuit 200 of FIG. 8 according to an embodiment of the present invention. Accordingly, as illustrated in FIG. 9, circuit 300 includes an APD (SSPM) 302 having a substrate 303 connected to a switch 304. A charge integration amplifier 330 may be positioned between APD (SSPM) 302 and switch 304. With a capacitor 332 of charge integration amplifier 330 sized appropriately at, for instance, 20 pF, charge integration amplifier 330 may be operable for both photon counting and energy integrating modes of operation of circuit 300. Furthermore, in order to further share components, a switch 334 may be included in circuit 300. Circuit 300 includes photon counting electronics 336, and energy integrating electronics 338. However, a common A/D converter 337 may be employed by appropriately separating electronics 336, 338, and operating a switch 334 in tandem with switch 304. Accordingly, to operate in photon counting mode, switch 304 is positioned at position 340 and switch 334 is positioned at position 344, thereby directing analog signals from APD (SSPM) 302 through photon counting electronics 336 to common A/D converter 337. Likewise, to operate in charge integrating mode, switch 304 is positioned at position 342 and switch 334 is positioned at position 346, thereby directing analog signals from APD (SSPM) 302 through energy integrating electronics 338 to common A/D converter 337. As such, a common charge integration amplifier 330 and a common A/D converter 337 may be employed in circuit 300, reducing the number of components thereof.

Therefore, according to one embodiment of the present invention, an imaging system includes a gantry having a bore therethrough designed to receive a patient being translated through the bore an x-ray source disposed in the gantry and configured to emit x-rays toward the patient, and a detector module disposed in the gantry to receive x-rays attenuated by the patient. The detector module includes a scintillator configured to absorb the x-rays and to convert the x-rays into optical photons, a device configured to receive the optical photons and to convert the optical photons to electrical signals, and an adaptive data acquisition system (DAS) configured to switch an operating mode of the device from a charge integrating mode to a photon counting mode, and vice versa.

In accordance with another embodiment a detector module includes a data acquisition system (DAS) configured to automatically switch operation of a solid-state photomultiplier (SSPM) between an energy integrating mode and a photon counting mode and automatically switch operation of the SSPM between the photon counting mode and the energy integrating mode.

In accordance with yet another embodiment of the present invention, a method for constructing a detector includes the steps of forming a scintillator to receive x-rays and convert the x-rays into optical photons, optically coupling a solid-state photomultiplier (SSPM) to the scintillator, the SSPM configured to receive and convert the optical photons into a corresponding electrical signal output, electrically connecting a data acquisition system (DAS) to the SSPM to receive the electrical signal output therefrom, and configuring the DAS to automatically switch operation of the SSPM between a charge integrating mode and a photon counting mode, and vice versa.

The present invention has been described in terms of the preferred embodiment, and it is recognized that equivalents, alternatives, and modifications, aside from those expressly stated, are possible and within the scope of the appending claims.

What is claimed is:

1. An imaging system comprising:
   a gantry having a bore therethrough designed to receive a patient being translated through the bore;
   an x-ray source disposed in the gantry and configured to emit x-rays toward the patient; and
   a detector module disposed in the gantry to receive x-rays attenuated by the patient, the detector module comprising:
      a scintillator configured to absorb the x-rays and to convert the x-rays into optical photons;
      a device configured to receive the optical photons and to convert the optical photons to electrical signals; and
      an adaptive data acquisition system (DAS) configured to switch an operating mode of the device from a charge integrating mode to a photon counting mode, and vice versa.

2. The imaging system of claim 1 wherein the imaging system comprises one of a CT, x-ray, RAD, and mammography system.

3. The imaging system of claim 1 wherein the adaptive DAS comprises a charge integrating circuit and a photon counting circuit that share at least one common electronic element.

4. The imaging system of claim 1 wherein the adaptive DAS is further configured to switch the operating mode of the device from the photon counting mode to the charge integrating mode if a maximum count rate exceeds $C_{max}$.

5. The imaging system of claim 4 wherein the operating mode is switched if the maximum count rate exceeds $C_{max}$ for at least two views.

6. The imaging system of claim 4 wherein $C_{max}$ is approximately $2 \times 10^7$ cps.

7. The imaging system of claim 1 wherein the adaptive DAS is configured to switch the operating mode of the device from the charge integrating mode to the photon counting mode if a signal charge decreases to less than $Q_{min}$.

8. The imaging system of claim 7 wherein the operating mode is switched if the signal charge decreases to less than $Q_{min}$ for at least two views.

9. The imaging system of claim 7 wherein $Q_{min}$ is calculated as:

$$Q_{min} = H * C_{max} * Q_0 * V.$$

10. The imaging system of claim 1 wherein the adaptive DAS is configured to switch between single views.

11. The imaging system of claim 1 wherein the adaptive DAS is configured to switch between scans.

12. The imaging system of claim 1 wherein the scintillator is a pixelated single crystal scintillation element.

13. The imaging system of claim 1 wherein the scintillator comprises a ceramic material having a decay time of approximately less than 50 nanoseconds.

14. The imaging system of claim 13 wherein the ceramic material comprises one of LYSO, LaBr$_3$, and (Lu$_x$Tb$_{1-x-y}$Ce$_y$)$_3$Al$_5$O$_{12}$ (i.e., LuTAG), where "x" ranges from 0.5 to 1.5 and "y" ranges from 0.01 to 0.15.

15. The imaging system of claim 1 wherein the scintillator comprises a material having a response time of approximately less than 20 nanoseconds.

16. The imaging system of claim 1 wherein the device comprises a solid-state photomultiplier (SSPM) pixel having an array of microcells configured to operate in Geiger-mode and to produce electrical charges upon receiving the optical photons.

17. A detector module comprising:
    a data acquisition system (DAS) configured to automatically switch operation of a solid-state photomultiplier (SSPM) between an energy integrating mode and a photon counting mode and automatically switch operation of the SSPM between the photon counting mode and the energy integrating mode.

18. The detector module of claim 17 further comprising:
    the SSPM configured to receive optical photons and to convert the optical photons to electrical signals; and
    a device to receive x-rays and convert the x-rays into optical photons.

19. The detector module of claim 18 wherein the x-rays received are from one of a CT, x-ray, RAD, and mammography system imaging system.

20. The detector module of claim 18 wherein the device comprises a ceramic scintillator.

21. The detector module of claim 17 wherein the DAS is configured to switch operation of the SSPM from the photon counting mode to the energy integrating mode if a maximum count rate exceeds $C_{max}$ for at least two CT views.

22. The detector module of claim 21 wherein $C_{max}$ is approximately $2 \times 10^7$ cps.

23. The detector module of claim 17 wherein the DAS is further configured to switch operation of the SSPM from the energy integrating mode to the photon counting mode if a signal charge decreases to less than $Q_{min}$ for at least two views.

24. The detector module of claim 23 wherein $Q_{min}$ is calculated as:

$$Q_{min} = H * C_{max} * Q_0 * V.$$

25. The detector module of claim 17 wherein the SSPM further comprises an array of microcells configured to operate in Geiger-mode and to produce electrical charges upon receiving optical photons.

26. A method for constructing a detector, the method comprising the steps of:
    forming a scintillator to receive x-rays and convert the x-rays into optical photons;
    optically coupling a solid-state photomultiplier (SSPM) to the scintillator, the SSPM configured to receive and convert the optical photons into a corresponding electrical signal output;
    electrically connecting a data acquisition system (DAS) to the SSPM to receive the electrical signal output therefrom; and
    configuring the DAS to automatically switch operation of the SSPM between a charge integrating mode and a photon counting mode, and vice versa.

27. The method of claim 26 wherein the detector comprises a CT detector.

28. The method of claim 26 wherein the step of configuring comprises configuring the DAS to automatically switch operation of the SSPM from the photon counting mode to the charge integrating mode if a maximum count rate exceeds $C_{max}$ for at least two views.

29. The method of claim 28 wherein $C_{max}$ is approximately $2 \times 10^7$ cps.

30. The method of claim 17 wherein the step of configuring comprises configuring the DAS to automatically switch operation of the SSPM from the charge integrating mode to the photon counting mode if a signal charge decreases to less than $Q_{min}$ for at least two views.

31. The method of claim 30 wherein $Q_{min}$ is calculated as:

$$Q_{min} = H * C_{max} * Q_0 * V.$$

* * * * *